US00PP18964P2

(12) United States Plant Patent
Smith

(10) Patent No.: US PP18,964 P2
(45) Date of Patent: Jun. 24, 2008

(54) ***HIBISCUS* PLANT NAMED 'CINNAMON GRAPPA'**

(50) Latin Name: ***Hibiscus* hybrid**
Varietal Denomination: Cinnamon Grappa

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,532

(22) Filed: Dec. 18, 2006

(51) Int. Cl.
*A01H 5/00* (2006.01)

(52) U.S. Cl. ..... Plt./257

(58) Field of Classification Search ..... Plt./257
See application file for complete search history.

(56) References Cited

PUBLICATIONS

UPOV ROM GTITM Computer Database, GTI Jouve Retrieval Software 2007/02 Citation for 'Cinnamon Grappa'.*

* cited by examiner

*Primary Examiner*—Wendy C. Haas
(74) *Attorney, Agent, or Firm*—C. A. Whealy

(57) ABSTRACT

A new and distinct cultivar of Hardy *Hibiscus* plant named 'Cinnamon Grappa', characterized by its upright and outwardly spreading plant habit; green-colored leaves that are palmately lobed; early flowering habit; and large single red purple-colored flowers.

1 Drawing Sheet

Botanical designation: *Hibiscus* hybrid.
Cultivar denomination: 'Cinnamon Grappa'.

BACKGROUND OF THE INVENTION

The present invention relates to a new and distinct cultivar of *Hibiscus,* botanically known as *Hibiscus* hybrid, commercially referred to as Hardy *Hibiscus* and hereinafter referred to by the name 'Cinnamon Grappa'.

The new *Hibiscus* is a product of a planned breeding program conducted by the Inventor in Alva, Fla. The objective of the breeding program is to create new freely-branching Hardy *Hibiscus* cultivars with a compact plant habit and desirable flower color.

The new Hardy *Hibiscus* originated from a cross-pollination made by the Inventor in Alva, Fla. during the summer of 2001, of an unnamed seedling selection of *Hibiscus* hybrid, not patented, as the female, or seed, parent with the *Hibiscus* hybrid cultivar Fantasia, disclosed in U.S. Plant Pat. No. 11,853, as the male, or pollen, parent. The cultivar Cinnamon Grappa was discovered and selected by the Inventor as a flowering plant within the progeny of the stated cross-pollination in a controlled environment in Alva, Fla. on Apr. 1, 2002.

Asexual reproduction of the new Hardy *Hibiscus* by vegetative terminal cuttings in a controlled environment in Alva, Fla. since May, 2002, has shown that the unique features of this new Hardy *Hibiscus* are stable and reproduced true to type in successive generations.

SUMMARY OF THE INVENTION

The cultivar Cinnamon Grappa has not been observed under all possible environmental conditions. The phenotype may vary somewhat with variations in environment and cultural practices such as temperature and light intensity without, however, and variance in genotype.

The following traits have been repeatedly observed and are determined to be the unique characteristics of 'Cinnamon Grappa'. These characteristics in combination distinguish 'Cinnamon Grappa' as a new and distinct cultivar of Hardy *Hibiscus:*

1. Upright and outwardly spreading plant habit
2. Green-colored leaves that are palmately lobed.
3. Early flowering habit.
4. Large single red purple-colored flowers.

Plants of the new Hardy *Hibiscus* can be compared to plants of the female parent selection. In side-by-side comparisons conducted in Alva, Fla., plants of the new Hardy *Hibiscus* differed from plants of the female parent selection in the following characteristics:

1. Plants of the new Hardy *Hibiscus* were more freely branching and denser than plants of the female parent selection.
2. Plants of the new Hardy *Hibiscus* and the female parent selection differed in leaf form and color.
3. Plants of the new Hardy *Hibiscus* flowered slightly later than plants of the female parent selection.
4. Flowers of plants of the new Hardy *Hibiscus* and the female parent selection differed in flower color.

Plants of the new Hardy *Hibiscus* can be compared to plants of the male parent, the cultivar Fantasia. In side-by-side comparisons conducted in Alva, Fla., plants of the new Hardy *Hibiscus* differed from plants of the cultivar Fantasia in the following characteristics:

1. Plants of the new Hardy *Hibiscus* were taller than plants of the cultivar Fantasia.
2. Plants of the new Hardy *Hibiscus* were more freely branching and denser than plants of the cultivar Fantasia.
3. Plants of the new Hardy *Hibiscus* and the cultivar Fantasia differed in leaf color.

4. Plants of the new Hardy *Hibiscus* flowered earlier than plants of the cultivar Fantasia.
5. Plants of the new Hardy *Hibiscus* had larger flowers than plants of the cultivar Fantasia.
6. Plants of the new Hardy *Hibiscus* and the cultivar Fantasia differed in flower color.

Plants of the new Hardy *Hibiscus* can be compared to plants of the *Hibiscus* hybrid cultivar Fireball, disclosed in U.S. Plant Pat. No. 13,631. In side-by-side comparisons conducted in Alva, Fla., plants of the new Hardy *Hibiscus* differed from plants of the cultivar Fireball in the following characteristics:

1. Plants of the new Hardy *Hibiscus* were shorter than plants of the cultivar Fireball.
2. Plants of the new Hardy *Hibiscus* were more freely branching and denser than plants of the cultivar Fireball.
3. Plants of the new Hardy *Hibiscus* and the cultivar Fireball differed in leaf form and color.
4. Plants of the new Hardy *Hibiscus* flowered earlier than plants of the cultivar Fireball.
5. Plants of the new Hardy *Hibiscus* had larger flowers than plants of the cultivar Fireball.

BRIEF DESCRIPTION OF THE PHOTOGRAPHS

The accompanying colored photographs illustrate the overall appearance of the new Hardy *Hibiscus,* showing the colors as true as it is reasonably possible to obtain in colored reproductions of this type. Colors in the photographs may differ slightly from the color values cited in the detailed botanical description which accurately describe the colors of the new Hardy *Hibiscus.*

The photograph at the bottom of the sheet comprises a side perspective view of a typical flowering plant of 'Cinnamon Grappa' grown in a container.

The photograph at the top of the sheet comprises a close-up view of a typical flower of 'Cinnamon Grappa'.

DETAILED BOTANICAL DESCRIPTION

The aforementioned photographs and following observations, measurements and values describe plants grown during the summer in Alva, Fla. in 1.5-gallon containers in a polypropylene-covered shadehouse and under conditions which closely approximate commercial Hardy *Hibiscus* production. During the production of the plants, day temperatures ranged from about 29° C. to about 35° C. and night temperatures ranged from about 21° C. to about 24° C. Plants were pinched one time and were about two months old when the photographs and the description were taken. In the description, color references are made to The Royal Horticultural Society Colour Chart, 1995 Edition, except where general terms of ordinary dictionary significance are used.

Botanical classification: *Hibiscus* hybrid cultivar Cinnamon Grappa.

Parentage:

*Female, or seed, parent.*—Unnamed seedling selection of *Hibiscus* hybrid, not patented.

*Male or pollen parent.*—*Hibiscus* hybrid cultivar Fantasia, disclosed in U.S. Plant Pat. No. 11,853.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick becoming fibrous and enlarged; white in color.

*Rooting habit.*—Freely branching.

Plant description:

*Plant form and growth habit.*—Upright and outwardly spreading plant habit. Vigorous growth habit.

*Branching habit.*—Freely branching, usually about four lateral branches develop after pinching.

*Plant height.*—About 35 cm.

*Plant diameter* (*area of spread*).—About 35 cm.

Lateral branch description:

*Length.*—About 28 cm.

*Diameter.*—About 1.1 cm.

*Internode length.*—About 1.6 cm.

*Strength.*—Strong.

*Texture.*—Smooth, glabrous.

*Color.*—146A.

Foliage description:

*Arrangement.*—Alternate, single.

*Length.*—About 13.3 cm.

*Width.*—About 10.8 cm.

*Shape.*—Palmately lobed, mapleleaf-shaped.

*Apex.*—Acuminate; reflexing.

*Base.*—Cordate.

*Margin.*—Irregular shallow lobing.

*Texture, upper and lower surfaces.*—Smooth, glabrous.

*Venation pattern.*—Palmate.

*Color.*—Developing and fully expanded foliage, upper surface: 147A; venation, 177A to 177B. Developing and fully expanded foliage, lower surface: 147B; venation, 146C.

*Petiole.*—Length: About 5.8 cm. Diameter: About 4 mm. Texture, upper and lower surfaces: Smooth, glabrous. Color, upper surface: 146B tinted with 177C. Color, lower surface: 146B.

Flower description:

*Flower arrangement.*—Flowers arranged singly originating from leaf axils. Lateral stems with typically one open flower and about eight flower buds. Flowers face mostly outwardly.

*Flower appearance.*—Large, rounded red purple-colored flowers. Flowers last for about four days. Flowers persistent. Flowers not fragrant.

*Natural flowering season.*—Usually spring and summer or during periods of warm weather. Early flowering habit, plants begin flowering about nine weeks after pinching.

*Flower diameter.*—About 15.8 cm.

*Flower length* (*height*).—About 4.6 cm.

*Flower bud.*—Length: About 4.5 cm. Diameter: About 2.6 cm. Shape: Ovate. Color: 72A.

*Petals.*—Arrangement: Corolla consists of five petals that are fused at base; petals imbricate. Length: About 5.2 cm. Width: About 6.3 cm. Shape: Obovate to fan-shaped. Apex: Rounded. Base: Acute. Margin: Entire. Texture: Upper surface: Smooth, glabrous; slightly ridge. Lower surface: Smooth, glabrous; veins prominent. Color: When opening, upper surface: 54A. When opening, lower surface: 70B. Fully opened, upper surface: 71B; towards the base, 67A;

at base, 155D. Fully opened, lower surface: 63B; towards the base, 155D; venation, 63A.

*Sepals.*—Appearance: Five sepals fused at the base into a star-shaped calyx. Length: About 1.7 cm. Width: About 1.3 cm. Shape: Elliptic to ovate. Apex: Acuminate. Margin: Entire. Texture, upper surface: Smooth, glabrous. Texture, lower surface: Sparsely pubescent. Color, upper surface: Close to 144A to 144B. Color, lower surface: Close to 144A.

*Bracts.*—Appearance: About ten fused at base. Length: About 1.8 cm. Width: About 2.5 mm. Shape: Lanceolate. Apex: Acute. Margin: Entire; curved upwards. Texture, upper and lower surfaces: Smooth, glabrous. Color, upper and lower surfaces: Close to 144A.

*Peduncles.*—Length: About 4.2 cm. Diameter: About 3 mm. Angle: About 45° from vertical. Strength: Strong. Texture: Smooth, glabrous. Color: 146A tinged with 200D.

*Reproductive organs.*—Androecium: Stamen number: Numerous, about 100. Filament length: About 2.5 mm. Filament color: Close to 157A. Anther shape: Round. Anther length: About 1 mm. Anther color: Close to 159A. Amount of pollen: Scarce. Pollen color: Close to 159A. Gynoecium: Pistil length: About 2.6 cm. Style length: About 2 cm. Style color: 162C. Stigma appearance: Flat; five-lobed. Stigma color: 56A. Ovary color: Close to 145D.

*Seed/fruit.*—Seed and fruit production has not been observed.

Low temperature tolerance: Plants of the new Hardy *Hibiscus* have been observed be hardy to USDA Zone 5.

Pathogen/pest resistance: Plants of the new Hardy *Hibiscus* have not been observed to be resistant to pathogens and pests common to Hardy *Hibiscus.*

It is claimed:

1. A new and distinct *Hibiscus* plant named 'Cinnamon Grappa' as illustrated and described.

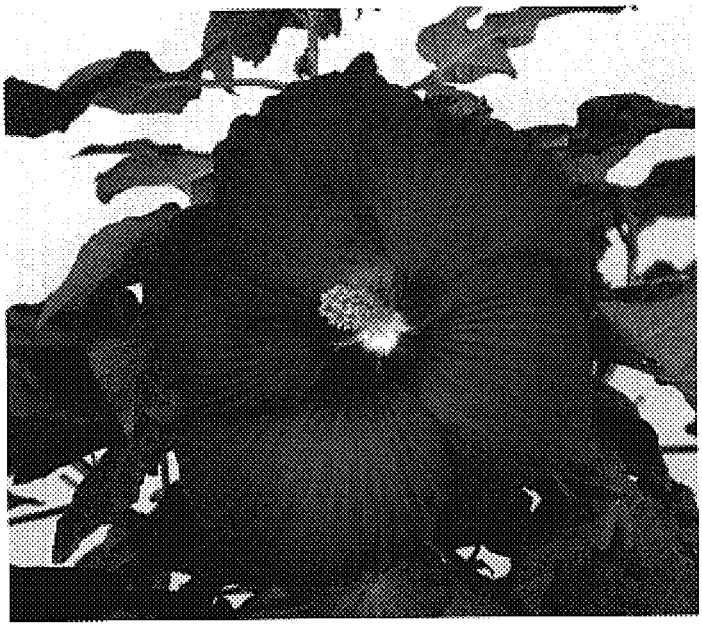
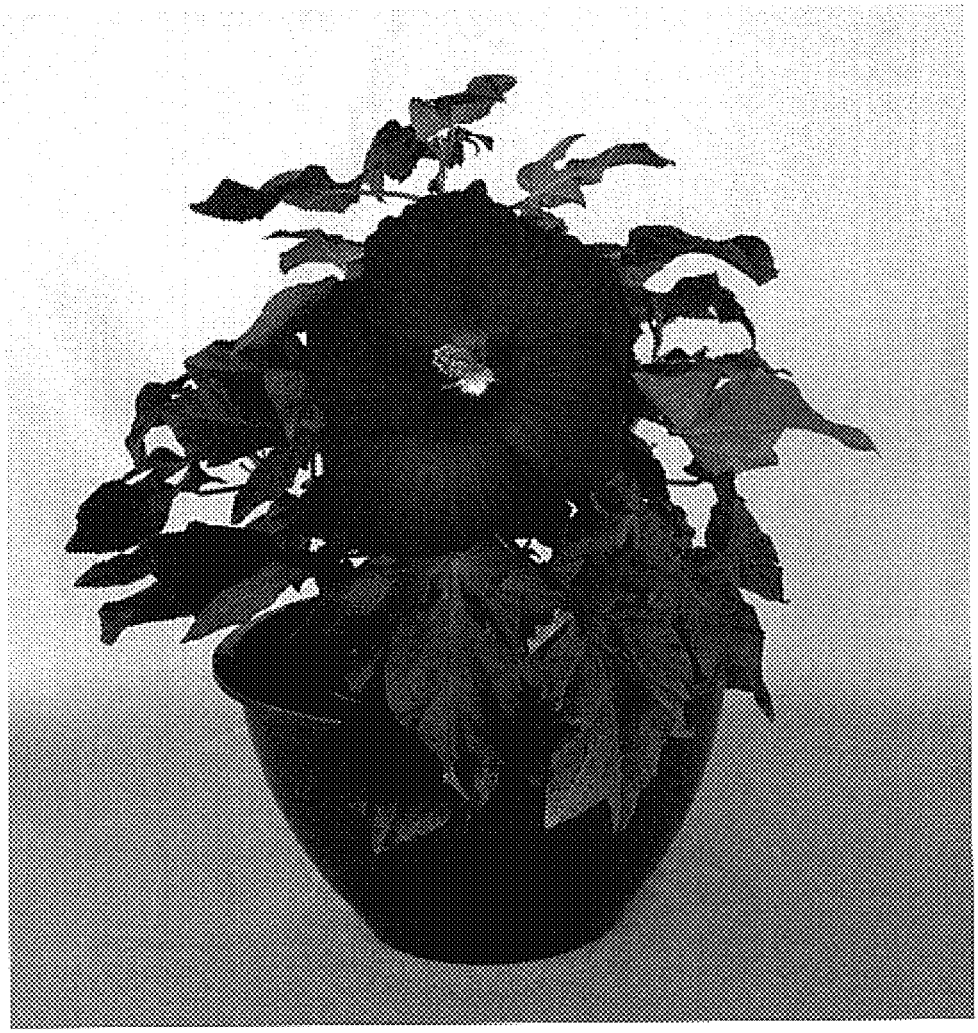

* * * * *